United States Patent
Saito et al.

(10) Patent No.: US 7,241,987 B2
(45) Date of Patent: Jul. 10, 2007

(54) PROBE FOR NEAR-FIELD MICROSCOPE, THE METHOD FOR MANUFACTURING THE PROBE AND SCANNING PROBE MICROSCOPE USING THE PROBE

(75) Inventors: Yuika Saito, Saitama (JP); Takashi Murakami, Saitama (JP); Satoshi Kawata, Saitama (JP); Yasushi Inoue, Saitama (JP); Kazuhito Tsukagoshi, Saitama (JP); Masato Iyoki, Chiba (JP)

(73) Assignees: Riken (JP); SII NanoTechnology Inc. (JP)

( * ) Notice: Subject to any disclaimer, the term of this patent is extended or adjusted under 35 U.S.C. 154(b) by 0 days.

(21) Appl. No.: 11/196,104

(22) Filed: Aug. 3, 2005

(65) Prior Publication Data
US 2006/0043276 A1 Mar. 2, 2006

(30) Foreign Application Priority Data
Sep. 2, 2004 (JP) ............................. 2004-255133

(51) Int. Cl.
*H01J 3/14* (2006.01)
*H01J 5/16* (2006.01)
*H01J 40/14* (2006.01)
*G01N 23/00* (2006.01)
*G21K 7/00* (2006.01)

(52) U.S. Cl. ...................... 250/234; 250/309; 356/501; 977/849; 977/862

(58) Field of Classification Search ................ 250/234, 250/306–311; 356/501; 73/105; 977/849–893; 427/166
See application file for complete search history.

(56) References Cited

U.S. PATENT DOCUMENTS 5,489,774 A * 2/1996 Akamine et al. ........... 250/234

* cited by examiner

*Primary Examiner*—Francis M. LeGasse, Jr.
(74) *Attorney, Agent, or Firm*—Adams & Wilks

(57) ABSTRACT

In a manufacture of a probe for a scattering type near-field microscope, there is provided a method of coating, with a high reproducibility, uniform metal particles efficiently inducing a surface enhanced Raman scattering. It has been adapted such that, in the probe for the scattering type near-field microscope, one part or all of the probe due to an interaction of at least an evanescent field is coated by metal particles which don't mutually adhere and have a particle diameter of 10 nm or larger and 50 nm or smaller in radius of curvature.

4 Claims, 10 Drawing Sheets

PROBE FOR NEAR-FIELD MICROSCOPE, THE METHOD FOR MANUFACTURING THE PROBE AND SCANNING PROBE MICROSCOPE USING THE PROBE

BACKGROUND OF THE INVENTION

1. Field of the Invention

The present invention relates to a probe for a near-field microscope in which a probe is caused to come close to or contact with an evanescent field generated on a sample surface, an evanescent light is scattered by a probe and, by detecting the scattered light by a photodetector, a local optical characteristic of the sample is measured with a resolution beyond diffraction limit of the incident light.

2. Description of the Related Art

In a conventional optical microscope, a spatial resolution has been limited to a length of about half of a used wavelength by the diffraction limit. However, in recent years, it becomes that a development in a technique called nano-technology is eagerly performed, and there is an increased demand for measuring the optical characteristic of a substance with the resolution exceeding the diffraction limit.

In order to realize the demand, a development in the near-field probe microscope is eagerly performed.

The conventional near-field probe microscope is classified into a fiber type and a scattering type.

In the fiber type near-field microscope, a tip of an optical fiber is sharpened, the size of an aperture is 100 nm or less, and portions other than the opening part is shielded from the light by a metal. When a laser is entered from an optical fiber aperture, the evanescent light is produced in the vicinity of the aperture. A probe approaches a sample by utilizing a shear force or an atomic force, which acts between a probe tip and the sample surface, the evanescent light irradiate the sample by measuring a near-field light intensity or a spectrum by the photodetector, the optical characteristic of the sample surface is measured with the resolving power exceeding the diffraction limit.

On the other hand, in the scattering type near-field microscope, the evanescent field is generated on the sample surface, the scattered light is generated by inserting the probe of a metal or a dielectric. The probe is inserted into the evanescent field and, by measuring the near-field light intensity or the spectra by the photodetector, the optical characteristic of the sample surface is measured with the resolving power beyond the diffraction limit.

The fiber type near-field microscope is the present measurement tool, the device is comparatively stable "it evaluates if the level of the background light is low"However, it is used in a fluorescence spectral analysis in which an excited light intensity is weak and a signal light intensity is comparatively easily obtained, an absorption measurement and the like, because a loss of the light in a taper portion inside the optical fiber cause the probe aperture to enlarge.

On the other hand, the scattering type near-field microscope can be used also in a Raman spectral analysis in which the scattering cross-sectional area is small and the signal light is difficult to detect and a nonlinear spectroscopy analysis, because it is possible to increase a incident light intensity imposed on the probe made from the metal or the dielectric and an electric field was enhanced by the interaction of the evanescent field both with incident light and the scattered light.

The scattering type near-field microscope of the prior art is explained on the basis of a schematic view of FIG. 9 (for example: Norihiko Hayazawa, Yasushi Inouye, Zouheir Sekkat, Satoshi Kawata, Near-field Raman scattering enhanced by a metallized tip, *Chemical Physics Letters*, 335, 369-374, 2001 (FIG. 1)).

A cantilever 101 is used for an interatomic force microscope, which has in its tip a probe 102 of a size of 40 nm in diameter and has been coated by silver 40 nm in thickness.

Further, by setting an objective lens 105 whose numerical aperture is 1.4 in a back side with respect to a measured face of a sample 103 through an oil-immersion oil 104 and entering an annular laser light 106 into a region in which the numerical aperture component of the objective lens 105 exceeds 1, the evanescent field is formed in a surface of the sample 103.

Next, the probe 102 is contacted with the evanescent field generation region of the sample 103 surface while performing a distance control by the interatomic force acting between the probe 102 and the sample 103 surface.

At this time, the evanescent field is scattered by the probe 102. By condensing this scattered light 107 by the same objective lens 105 (not shown in the drawing), an analysis of the local optical characteristic by the probe tip becomes possible.

In this prior art, rhotamine 6G that is one kind of dye is measured as the sample. In the scattered light from the sample Raman scattered light is generated also besides a Rayleigh scattered light whose wavelength is the same as the excited light.

Further, by the facts that a surface plasmon is excited in a surface of the silver coated probe 102 and that the sample 103 and the silver probe 102 tip are contacted, a so-called surface enhanced Raman scattering (SERS: Surface Enhanced Raman Scattering) occurs, so that it becomes possible to enhance the Raman scattered light.

By condensing these scattered lights by the objective lens 105, removing the Rayleigh scattered light by a notch filter or the like and, after spectrally dispersing them by a spectroscope, detecting it by a liquid nitrogen cooled CCD, it is possible to obtain a local Raman spectra (the notch filter, the spectroscope and the CCD are not shown in the drawing).

An electron microscope photograph of the probe 102 provided in the cantilever 101 used in FIG. 9 is shown in FIG. 10.

The fact is seen that a silver particle of the probe 102 surface adheres to a probe surface like an island and has a longitudinally long shape. Further, in a tip portion 102a of the probe, the whole tip portion of the probe is covered by a uniform silver particle.

Next, FIG. 11-FIG. 13 and Table 1 are explained about the Raman spectral analysis.

Since a vibration spectroscopy mainly such as Raman spectroscopy can obtain a structural information in comparison with the fluorescence spectral analysis and the absorption measurement, it is possible to obtain detailed information concerning molecule vibration, orientation, intermolecular interaction, and excited state. However, since the Raman scattered light is generally very weak, its measurement is difficult. Especially, in a case where the excitation is performed by the evanescent light, the light quantity becomes weaker.

Therefore, in a case where the Raman spectroscopy is performed by scattering the evanescent field by the probe, a Raman signal is intended by utilizing the surface enhanced Raman scattering like the prior art mentioned above.

The surface enhanced Raman scattering is a phenomenon in which, by an electron excitation (surface plasmon) of a metal surface, a Raman scattering cross-section area concerning of the signal light from the metal surface is enhanced to about $10^5$ to $10^{10}$ times.

Accordingly, in order to efficiently induce the surface enhanced Raman scattering, a condition for efficiently exciting the surface plasmon is necessary.

And, an efficiency of the surface plasmon excitation largely depends on a kind of the metal and a size and a shape of the particle.

As to the metal, it is known that, in a visible light region silver is efficient.

Table 1 shows a value of an imaginary number part of a permittivity at a plasmon absorption maximum wavelength and an absorption maximum of a representative metal (refer to C. F. Bohren, D. R. Huffman, Absorption and Scattering of Light by Small Particles, Wiley 1983 (Table 12-1)).

TABLE 1

| Metal kind | Bulk plasmon energy (eV) | Surface plasmon energy (eV) | Permittivity: $\epsilon = \epsilon' + i \epsilon''$ (real part $\epsilon'$ = value of imaginary number part $\epsilon''$ at −2) |
|---|---|---|---|
| Lithium | 6.6 | 3.4 | 1.0 |
| Sodium | 5.4 | 3.3 | 0.12 |
| Potassium | 3.8 | 2.4 | 0.13 |
| Magnesium | 10.7 | 6.3 | 0.5 |
| Aluminum | 15.1 | 8.8 | 0.2 |
| Iron | 10.3 | 5.0 | 5.1 |
| Copper | — | 3.5 | 4.9 |
| Silver | 3.8 | 3.5 | 0.28 |
| Gold | — | 2.5 | 5.0 |
| Graphite | — | 5.5 | 2.7 |

From Table 1, among the metals having the absorption maximum in the visible light region, silver has the imaginary number part of the permittivity which is peculiarly small. This shows the fact that an attenuation of the plasmon is small and accordingly the silver is most excellent for the surface enhanced Raman scattering in the visible light region.

Further, an influence of a radius of curvature exerting on the absorption cross-sectional area of the silver is shown in FIG. 11, and an influence of the radius of curvature exerting on a near-field scattering efficiency in FIG. 12 (refer to S. Kawata ed, Near-Field Optics and Surface Plasmon Polaritons, Topics Appl. Phys. 81, 97-122 (2001) (FIG. 7, FIG. 8)).

From FIG. 11, it is apparent that the absorption cross-sectional area of the silver has a peak when a particle size is between 10 nm and 50 nm in radius, and becomes a maximum value when the radius is 10 to 20 nm. Since a light energy absorbed contributes to a plasmon excitation, the fact that the absorption cross-sectional area is large becomes the fact that an energy inducing the surface enhanced Raman scattering is large. Further, from FIG. 12, also a near-field scattering efficiency has a peak in a vicinity where the particle size is 10 nm to 50 nm in radius and becomes maximum when the radius is 20 nm, and in this region it is possible to efficiently scatter a near-filed light.

Additionally, in FIG. 13, there is shown a plasmon absorption efficiency depending on a shape of the silver particle (refer to Stockle R M, Deckert V, Fokas C, Zenobi R, Controlled formation of isolated silver islands for surface-enhanced Raman scattering, APPLIED SPECTROSCOPY 54 (11): 1577-1583 November 2000 (FIG. 2)).

Under a state that the silver particle has flatly adhered to a substrate, although the plasmon absorption is scarcely seen, if an island shape of the silver approaches a spherical shape by annealing the surface, a strong plasmon absorption appears. From this fact, for a plasmon induction it is desirable that the shape of the silver particle approximates to the spherical shape, not only its size.

Accordingly, in a case where the Raman spectral analysis is performed by using the near-field, by controlling the shape of the metal particle coated to the probe to a shape approximating to the spherical shape whose radius is 10 nm to 50 nm, it becomes possible to efficiently generate the surface plasmon and, as a result, the Raman scattered light is enhanced and it becomes possible to improve the sensitivity of a Raman spectroscopy. Additionally, by controlling the shape and the size of the metal particle, a quantitative experiment of a surface enhanced Raman scattering effect becomes possible. As a result, it becomes possible to quantitatively estimate the near-field Raman scattered light.

However, in the prior art, since there has not existed a method capable of controlling the shape and the size of the metal particle to optimum ones only by controlling a film thickness of the metal, which is represented by the silver, the gold and the like, coated to the probe, there was no reproducibility with respect to the shape or the size of the metal particle. Further, since an affinity between a substrate and a vapor-deposited metal is good, the vapor-deposited metal forms an island-like film in the vapor deposition object, so that it has been difficult to form a particle-like film.

For this reason, the surface enhanced Raman scattering effect in every probe largely differs, so that it has been impossible to perform from a Raman spectroscopy a quantitative analysis of a intensity.

SUMMARY OF THE INVENTION

Whereupon, an object of the invention is to improve, in the scattering type near-field microscope, the Raman spectral sensitivity by forming in the probe surface, with a high reproducibility, with metal particles which don't mutually adhere and whose radius of curvature is 10 nm or larger and 50 nm or smaller, desirably the particles of silver, silver alloy, gold or gold alloy, whose radius of curvature is 20 nm, and efficiently generating the surface plasmon to thereby intend enhanse the Raman scattered light.

In order to solve the above problems, in a probe for a near-field microscope of the invention, it has been made such a structure that one part or all of the probe due to an interaction of at least the evanescent field has been coated by metal particles which don't mutually adhere and have a particle diameter of 10 nm or larger and 50 nm or smaller in radius of curvature.

It has been adapted such that this probe is inserted into the evanescent field generated in the sample surface, the surface plasmon is excited by an interaction between the evanescent field and the metal particles by scattering the evanescent field by a probe tip, and enhancing a scattered light intensity by the surface enhanced Raman to thereby detect that scattered light.

Further, in the invention, there is manufactured a probe for a near-field microscope by vapor-depositing, as a first vapor deposition process, gold-palladium as a substrate metal to the probe, next vapor-depositing, as a second vapor deposition process, any metal of silver, silver alloy, gold and gold alloy onto a film of the gold-palladium, thereby forming, in one part or all of a probe surface, particles of the metal having been used in the second vapor deposition process, which don't mutually adhere and have a particle diameter of 10 nm or larger and 50 nm or smaller in radius of curvature, and adjusting a size of the radius of curvature of the metal particles by adjusting a vapor deposition time and a vapor deposition speed in the 2nd vapor deposition process.

Additionally, in the invention, there is contained at least a process for reducing silver nitrate to silver by adding an aqueous solution containing an aldehyde compound, such as glucose and folmaldehyde, as a reducing agent to an aqueous solution containing silver nitrate, and there is manufactured a probe for a near-field microscope by growing silver particles in a probe surface by immersing the probe into the mixed solution reducing silver nitrate to silver, forming, in one part or all of the probe surface, the silver particles which don't mutually adhere and have the particle diameter of 10 nm or larger and 50 nm or smaller in radius of curvature, and adjusting a size of the radius of curvature of the silver particles by adjusting a silver nitrate concentration and a time for immersing the probe into the mixed solution.

In the probe for the near-field microscope of the invention, one part or all of the probe due to the interaction of at least the evanescent field has been coated by the metal particles which don't mutually adhere and have the particle diameter corresponding to 10 nm to 50 nm in radius of curvature.

By this, in a case where the evanescent field is scattered by the probe apex, the surface plasmon is efficiently induced in the probe apex, and the Raman scattered light can be largely enhanced, so the it has become possible to improve the Raman spectral sensitivity. Additionally, even in a case where the probe is different, it becomes possible to obtain a stable surface enhanced Raman scattering effect by controlling the metal particle size, so that a quantitative measurement has become possible.

Further, by enhancing the Raman scattered light at the probe tip by the surface enhanced Raman scattering effect, a measurement in a region more minute than the prior art has become possible.

Further, in the method of manufacturing the probe of the invention, it has been adapted such that, as the first vapor deposition process, gold-palladium as the substrate metal is vapor-deposited to the probe and, next as the second vapor deposition process, any metal of silver, silver alloy, gold and gold alloy is vapor-deposited onto the film of the gold-palladium.

Like this, by using the gold-palladium in the substrate metal, it has become such that the substrate metal has an affinity optimum for forming the vapor-deposited metal in a particle-like form and, additionally by adjusting the time in the second vapor deposition process, it has become possible to form in one part or all of the probe surface, with the high reproducibility, the particles which don't mutually adhere and have the particle diameter of 10 nm or larger and 50 nm or smaller in radius of curvature.

Additionally, in the method of manufacturing the probe, there is contained at least the process for reducing silver nitrate to silver by adding the aqueous solution containing the aldehyde compound, such as glucose and folmaldehyde, as the reducing agent to the aqueous solution containing silver nitrate, and it has been adapted such that the silver particles are grown on the probe surface by immersing the probe into the mixed solution reducing silver nitrate to solution.

In the case of this method, by adjusting the silver nitrate concentration and the time for immersing the probe into the mixed solution, it has become possible to form in one part or all of the probe surface, with the high reproducibility, the silver particles which don't mutually adhere and have the particle diameter of 10 nm or larger and 50 nm or smaller in radius of curvature. This method is simpler in its equipment than means such as conventional vapor deposition or sputter, and it is also possible to decrease a probe manufacturing cost.

DETAILED DESCRIPTION OF THE INVENTION

Figure 1:
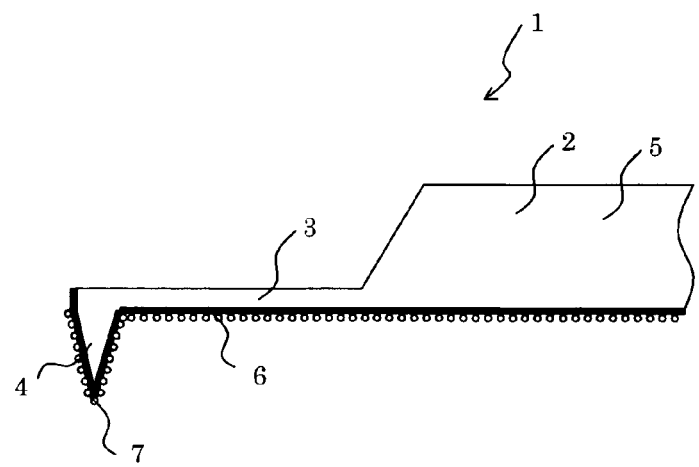
FIG. 1 is a schematic view of a probe for a near-field microscope according to a 1st embodiment of the invention.

Hereunder, it is detailedly explained about best modes for carrying out the invention by referring to the drawings.

EMBODIMENT 1

In FIG. 1, there is shown a schematic view of a probe 1 for a near-field microscope, which is a 1st embodiment of the invention. This is a sectional view cut along a center axis in a longitudinal direction of a cantilever part 3 of a cantilever 2 with a probe, which is made of silicon and generally marketed for a scanning probe microscope. This cantilever 2 with the probe has a probe body with a structure in which a probe 4 whose shape is a quadrangular pyramid and which is about 10 nm in tip radius and 20 μm in height is provided in a tip of the thin rectangle shape cantilever part 3 which is about 350 μm in length, 35 μm in width and 1 μm in thickness, and a support part 5 for fixing to a holder is provided in a tail end of the cantilever 3.

Figure 2:
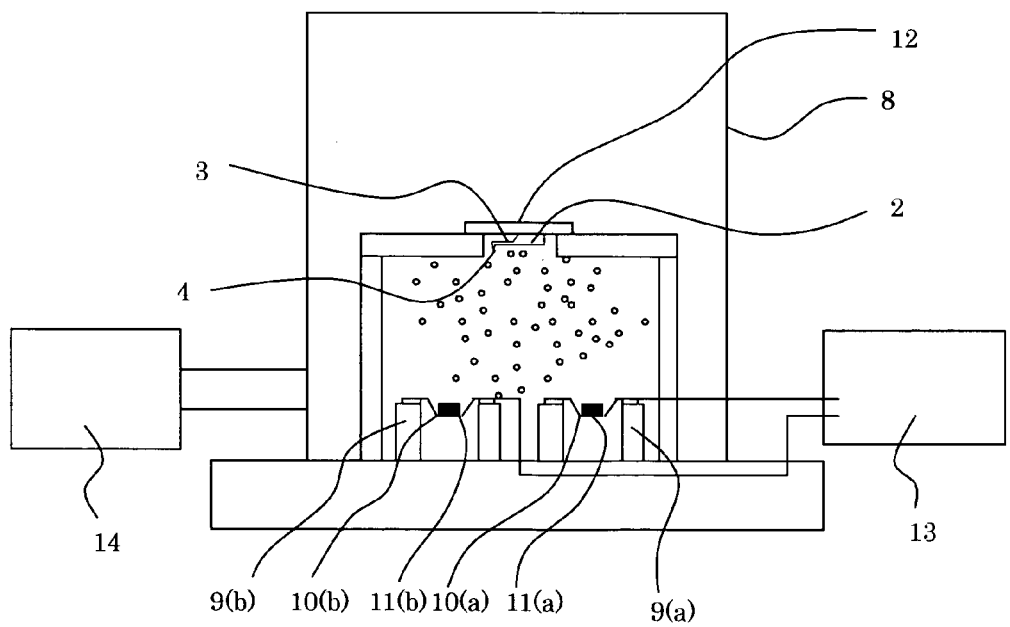
FIG. 2 is a schematic view of an apparatus for vapor-depositing a metal particle to the probe for the near-field microscope according to the 1st embodiment of the invention.

A block diagram of an apparatus for coating metal particles to a surface of the cantilever 2 with the probe is shown in FIG. 2. The apparatus is constituted by a bell-jar type vacuum chamber 8, vapor deposition source fixation parts 9(*a*) and 9(*b*), evaporation sources 10(*a*) and 10(*b*) becoming heaters by the fact that a current flows therein, two kinds of evaporation materials 11(*a*) and 11(*b*) for coating to the probe on the evaporation sources 10(*a*) and 10(*b*), the cantilever 2 with the probe whose probe 4 side has been disposed in such a direction as to be opposite to the evaporation materials 11(*a*) and 11(*b*), a cantilever fixation jig 12 fixing the cantilever 2 with the probe like the above, an electric source 13 capable of flowing the current by selecting either of the evaporation sources 10(*a*) and 10(*b*), and a vacuum pump 14 for evacuating the bell-jar type vacuum chamber.

Figure 3:
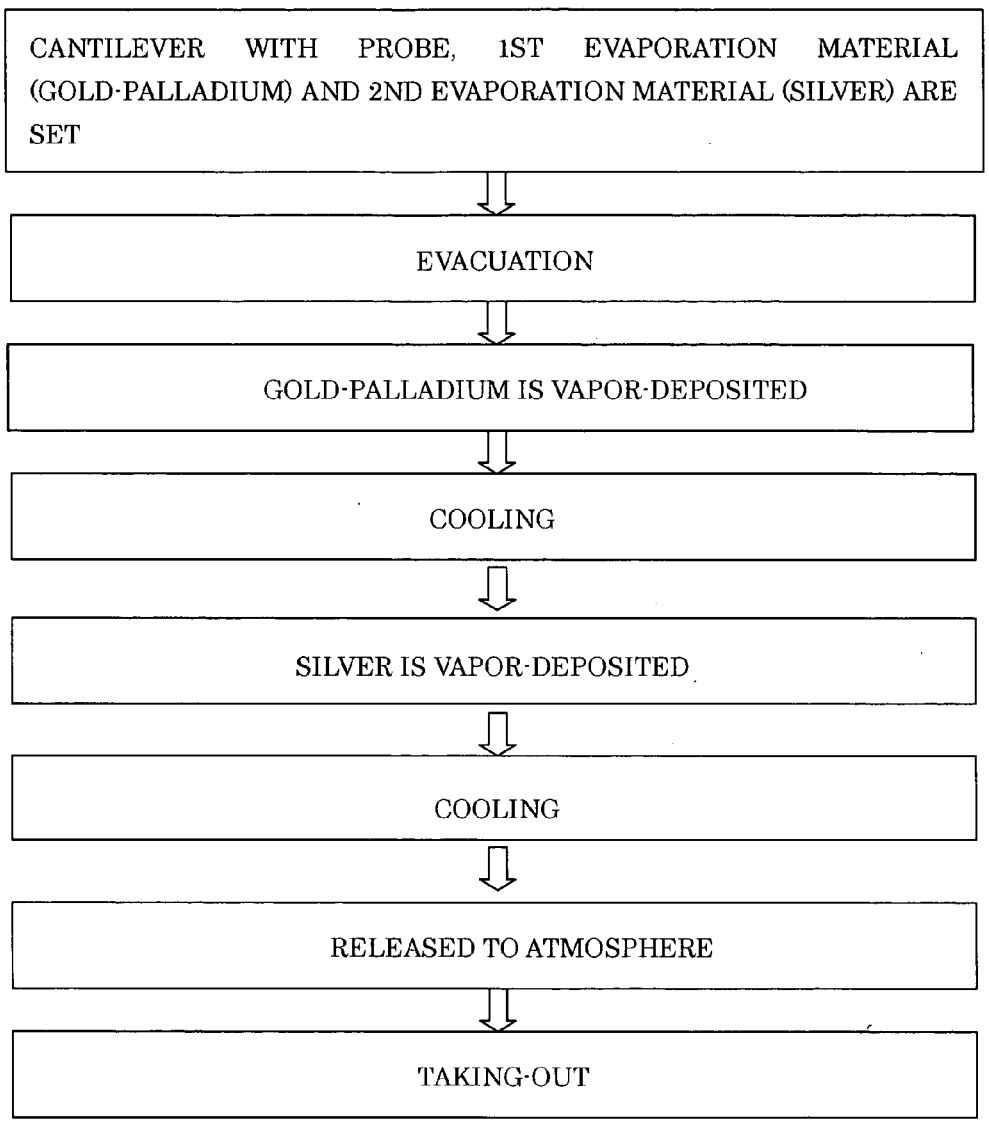
FIG. 3 is a flowchart of a method of manufacturing the probe for the near-field microscope according to the 1st embodiment of the invention.

In FIG. 3, there is shown a flowchart of a method of manufacturing the probe for the near-field microscope according to the first embodiment of the invention in a case where the apparatus of FIG. 2 has been used.

In the bell-jar type vacuum vapor deposition apparatus 8, the vapor deposition sources 10(*a*) and 10(*b*) comprising tungsten heaters fixed to the vapor deposition source fixation parts 9(*a*) and 9(*b*) are provided in two places. The evaporation materials 11(*a*) and 11(*b*) are disposed respectively on the evaporation sources 10(*a*) and 10(*b*) in two places. Here, gold-palladium has been used as the first evaporation material 11(*a*) becoming the substrate metal and, as to a component ratio, components of gold and palladium have been made respectively gold 80% and palladium 20%. Further, wire-like silver of 0.5 mm in diameter φ and 40 mm in length has been used as the second evaporation material 11(*b*). Next, the cantilever 2 with the probe is fixed to the cantilever fixation jig 12 in a position about 30 cm just above the evaporation sources 10(*a*) and 10(*b*) in such a direction that the probe 4 side is opposite to the evaporation sources 10(*a*) and 10(*b*).

Next, the bell-jar type vacuum chamber 8 is evacuated to a vacuum of $10^{-5}$ Torr or lower by using the vacuum pump 14. The vacuum pump is used by connecting a rotary pump or the like to a turbo-molecular pump or a diffusion pump.

Under a state that a degree of vacuum is $10^{-5}$ Torr or lower, the current is flowed to the evaporation source 10(*a*) by using the electric source 13. First, a current value is gradually increased from 0 A to 170 A by spending 2 minutes. Next, the current value of 170 A is kept, and the evaporation material 11(*a*) is vapor-deposited for 3 minutes to the cantilever 2 with the probe. By this first vapor deposition process becoming a formation of the substrate metal, a gold-palladium film 6 is coated to the probe 4 and the cantilever part 3 in a film thickness of about 5 nm.

After cooling for about 10 minutes, the current is flowed to the evaporation source 10(*b*) by using the electric source 13 with the degree of vacuum being kept to the state of $10^{-5}$ Torr or lower intact.

First, the current value is gradually increased from 0 A to 70 A by spending 1 minute. Next, under a state that 70 A has been maintained, all of the silver wire 11(*b*) on the evaporation source 10(*b*) is vapor-deposited to the cantilever 2 with the probe, on which the gold-palladium film has been formed in the 1st vapor deposition process, by spending 2 minutes. Thereafter, after cooling for 10 minutes with the vacuum being kept intact for preventing an oxidation, the vacuum is released to the atmosphere and the probe 1 for the near-field microscope is taken out.

In the present embodiment, by the fact that the gold-palladium is used in the substrate metal and the silver is vapor-deposited thereon, it follows that the substrate metal has the affinity optimum for forming the vapor-deposited metal like the particle and, as shown in FIG. 1, it has become such that silver particles 7 are formed without mutually adhering on a surface of the gold-palladium film 6 formed in the probe 4 and the cantilever part 3.

Further, by adjusting a vapor deposition time in a second vapor deposition process to 2 minutes, adjusting the heating current flowed to the tungsten heater 10(*b*) and performing the vapor deposition at a vapor deposition speed of 3 angstroms per second, it is possible to control the radius of curvature of the particle to 7 to 20 nm.

Figure 4:
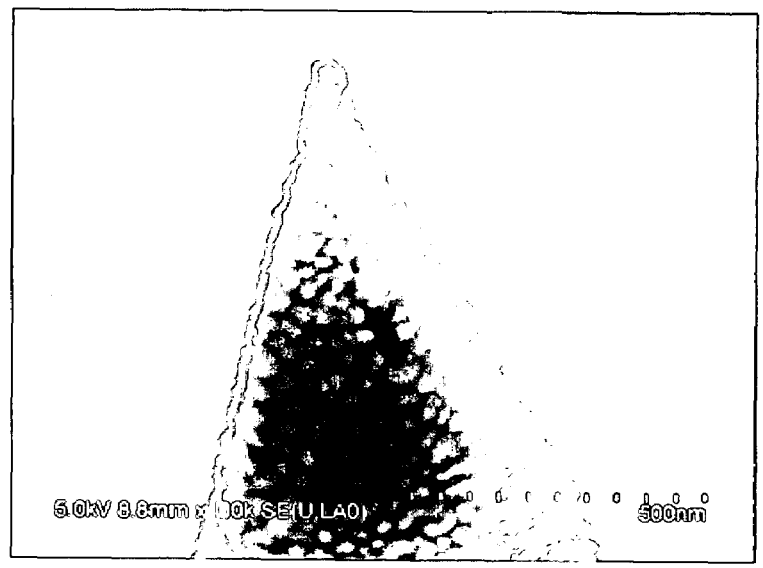
FIG. 4 is an scanning electron microscope photograph of the probe for the near-field microscope, which has been made by the 1st embodiment of the invention.

An scanning electron microscope photograph of the probe 1 for the near-field microscope, which has been made like the above, is shown in FIG. 4.

Here, as to a size of the silver particle 7, although about 20 nm in radius of curvature is optimum, if it is the particle whose radius of curvature is 10 nm or larger and 50 nm or smaller, it is possible to efficiently generate the surface enhanced Raman scattering, and the particle having a particle diameter of this range is included in the invention.

As to an ideal shape in the present manufacturing method, although the silver particles having a uniform particle diameter are formed in the probe part and the cantilever part in a shape approximating to spherical shape without mutually adhering, such a matter is considered as well that unavoidably one part of the particles don't become the prescribed shape or are adhered due to the shape of the probe or the cantilever, or an error in a disposed position. Also in this case, if one portion of the metal particles having been coated in the probe surface due to the interaction with a sample are formed in the prescribed shape without adhering, since it is possible to achieve the object of the invention, a probe in which one portion of the coated particles in the probe surface due to the interaction with the sample are 10 nm or larger and 50 nm or smaller in radius of curvature and have no adhesion is included in the invention.

Further, also as to the shape of the particle, ideally, although rather a shape approximating to the spherical shape is good, if it is constituted by the particles of 10 nm or larger and 50 nm or smaller in radius of curvature, it is possible to efficiently induce the surface enhanced Raman scattering, and it is included in the invention.

Further, the invention is not limited to the above parameters at a manufacturing time, and a probe in which any metal of silver, silver alloy, gold and gold alloy is vapor-deposited with the gold-palladium being used in the substrate, one part or all of the particles are 10 nm or larger and 50 nm or smaller in radius of curvature and no adhesion exists is included in the invention.

EMBODIMENT 2

Figure 5:
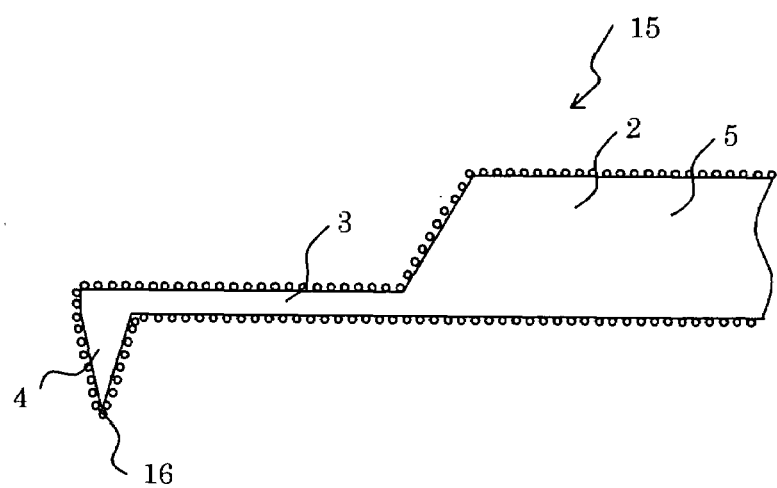
FIG. 5 is a schematic view of a probe for a near-field microscope according to a second embodiment of the invention.

In FIG. 5, there is shown a schematic view of a probe 15 for a near-field microscope, which is a second embodiment of the invention. FIG. 5 is a sectional view cut along the center axis in the longitudinal direction of the cantilever part 3 of the cantilever 2 with the probe, which is made of silicon. The material and the dimensions of the cantilever 2 with the probe are similar to the 1st embodiment. By a method mentioned later, approximately spherical silver particles 16 having been controlled to 20 nm in radius of curvature are coated to the surface of the cantilever 2 with the probe without mutually adhering.

Figure 6:
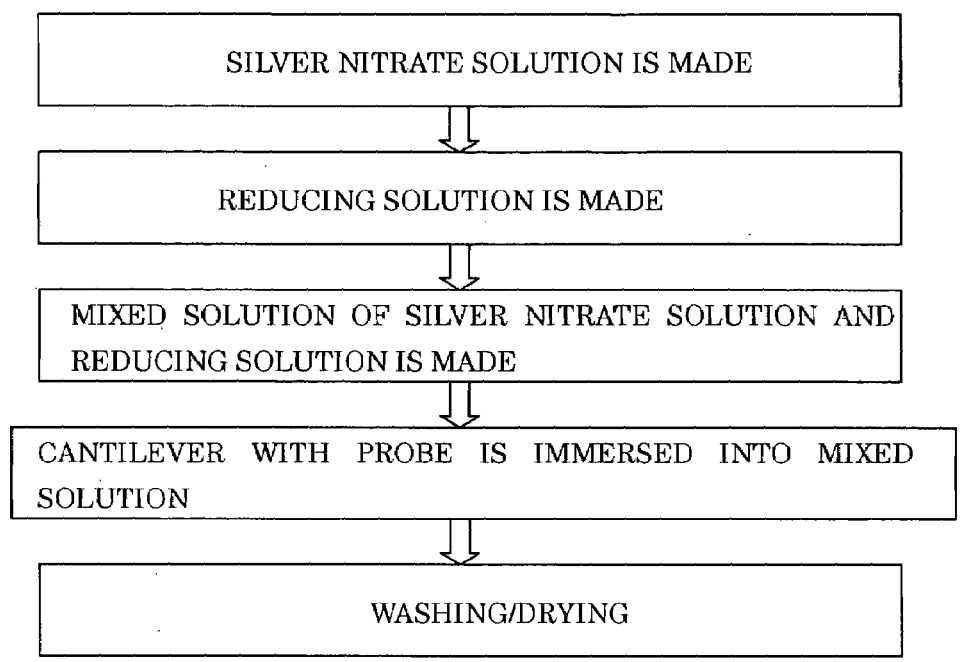
FIG. 6 is a flowchart showing a method of coating the probe for the near-field microscope according to the second embodiment of the invention.

In FIG. 6, there is shown a flowchart of a method of manufacturing the probe for the near-field microscope according to the second embodiment of the invention. A method of coating the silver particles is explained in compliance with this flowchart.

First, if a mixed solution is made by adding 3 ml of water to 90 μl of 6 percent weight of silver nitrate aqueous solution and 120 μl of 0.3 percent weight of potassium hydroxide in order to adjust pH, a minute brown precipitate of silver oxide occurs in the mixed solution. Next, 5 wt % ammonia solution is added by 10 μl at a time as a complex formation agent to this mixed solution till the brown precipitate forms ammonia complex to thereby completely dissolve. Additionally, 6 percent weight of silver nitrate aqueous solution is added by 10 μl at a time till an aqueous solution becomes thin yellow again.

Next, a reducing agent is made by mixing 0.5 ml of methanol and 1 ml of 35 percent weight of glucose aqueous solution, and it is kept in temperature at 35° C. before performing a reaction. And, a mixed solution is made by adding the above reducing solution to the above silver nitrate aqueous solution followed by mixing.

Figure 7:
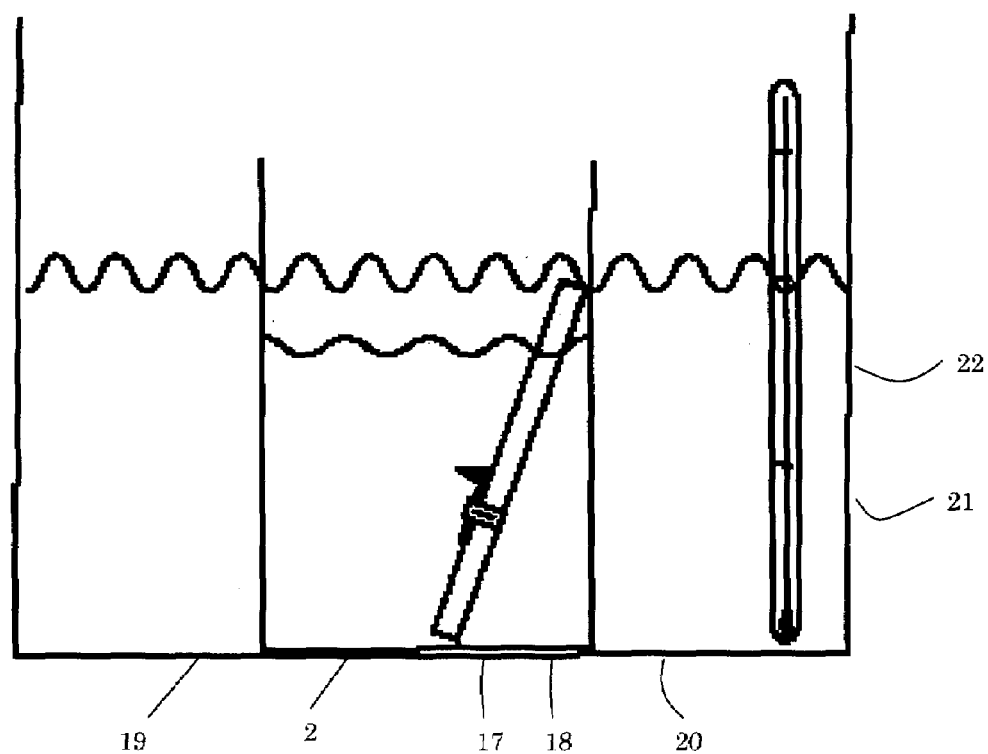
FIG. 7 is a schematic view showing the method of coating the probe for the near-field microscope according to the second embodiment of the invention.

In FIG. 7, there is shown a schematic view of a method of coating the probe. The cantilever 2 with the probe is fixed to a fixing jig 17, and immersed for about 120 second in a container 19 containing the above mixed solution 18. It has been adapted such that the container 19 is inserted into a container 21 containing a water 20, a temperature of the water 20 is kept at 35° C. by a thermometer 22, and the reaction is performed under this temperature environment.

Finally, the coated probe 15 for the near-field microscope is taken out of the mixed solution 18, washed by a mixed aqueous solution of acetone and water, and dried in a desiccator while being evacuated.

In the present embodiment, silver crystal nuclei in the mixed solution adhere to surfaces of the probe 4 and the cantilever 3 during the cantilever 2 with the probe is immersed in the mixed solution 18, and a crystal growth happens. At this time, by adjusting a concentration of silver nitrate and a time for immersing the cantilever 2 with the probe in the mixed solution, as shown in FIG. 5 it becomes possible to form the approximately spherical silver particles 16 having been controlled to 20 nm in radius of curvature onto the probe surface without mutually adhering.

Figure 8:
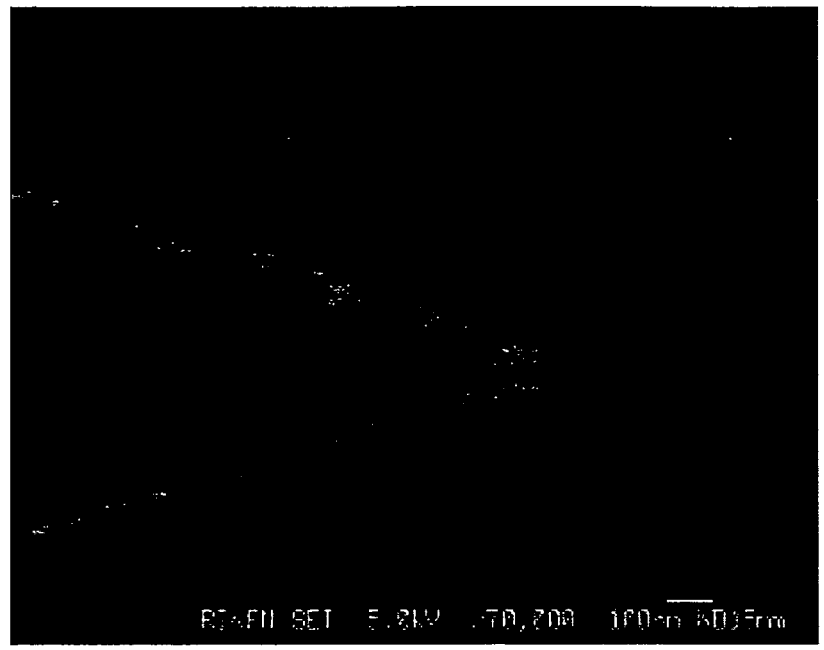
FIG. 8 is an electron microscope photograph of the probe for the near-field microscope, which has been made by the second embodiment of the invention.
Figure 9:
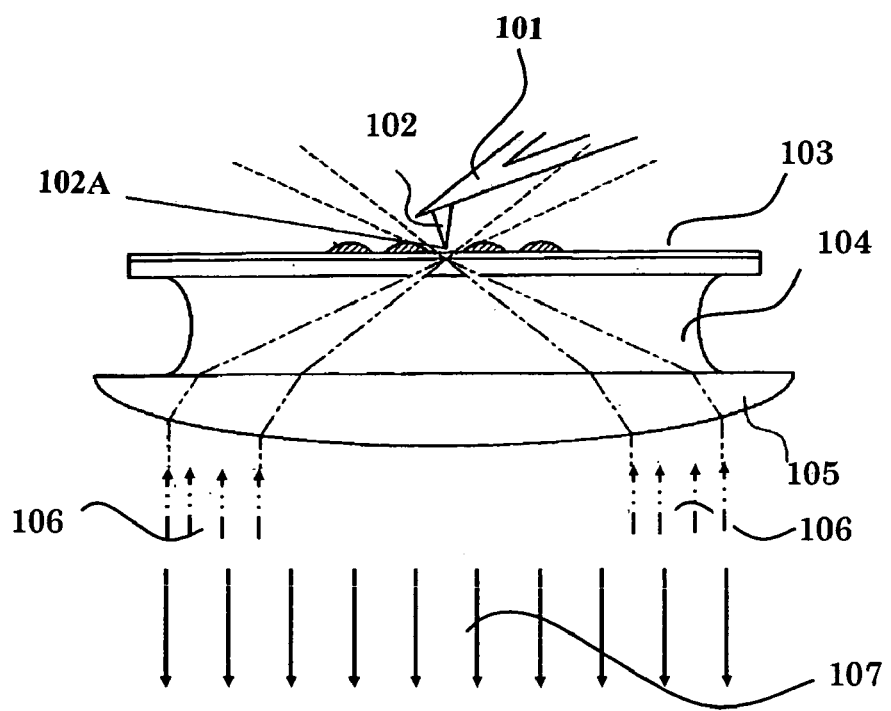
FIG. 9 is a schematic view of a scattering type near-field microscope of prior art.
Figure 10:
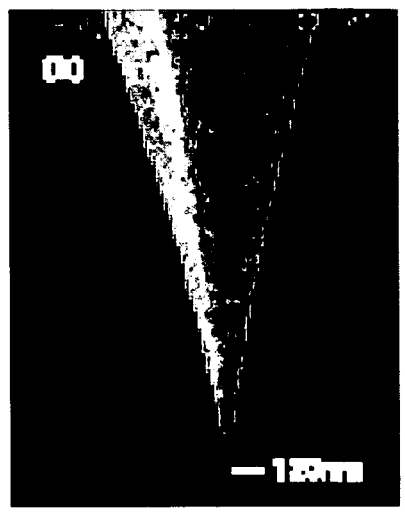
FIG. 10 is an scanning electron microscope photograph of a probe for a near-filed microscope of prior art.
Figure 11:
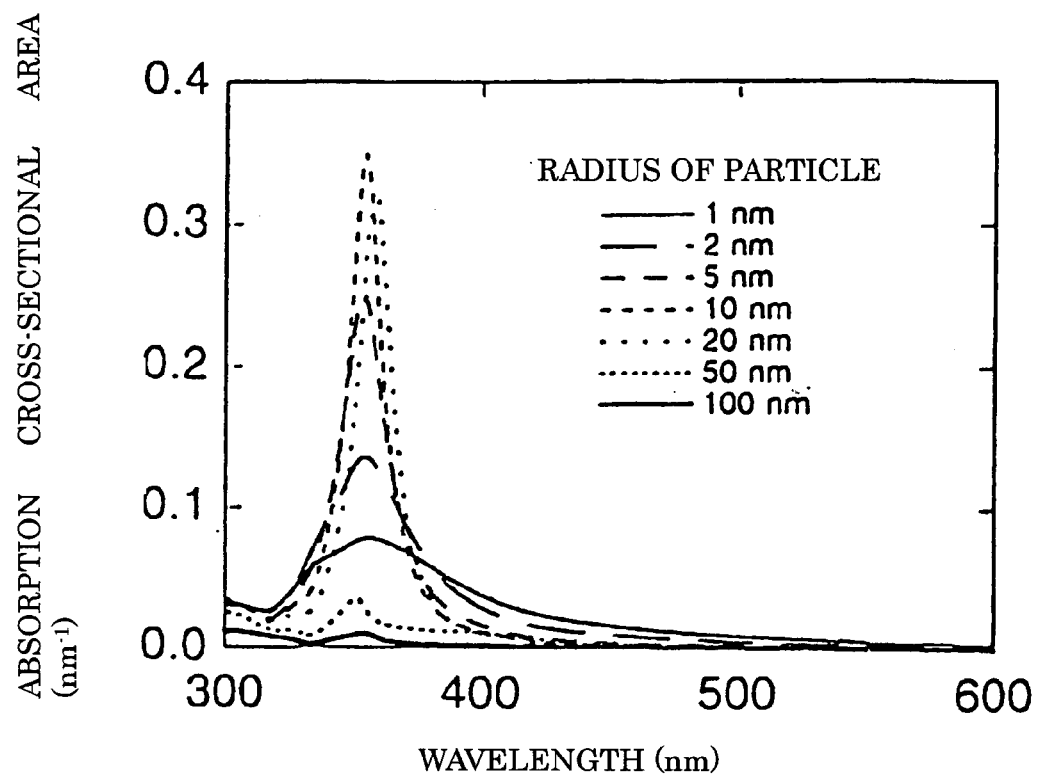
FIG. 11 is a graph showing an influence of a radius of curvature exerting on an absorption cross-sectional area of silver.
Figure 12:
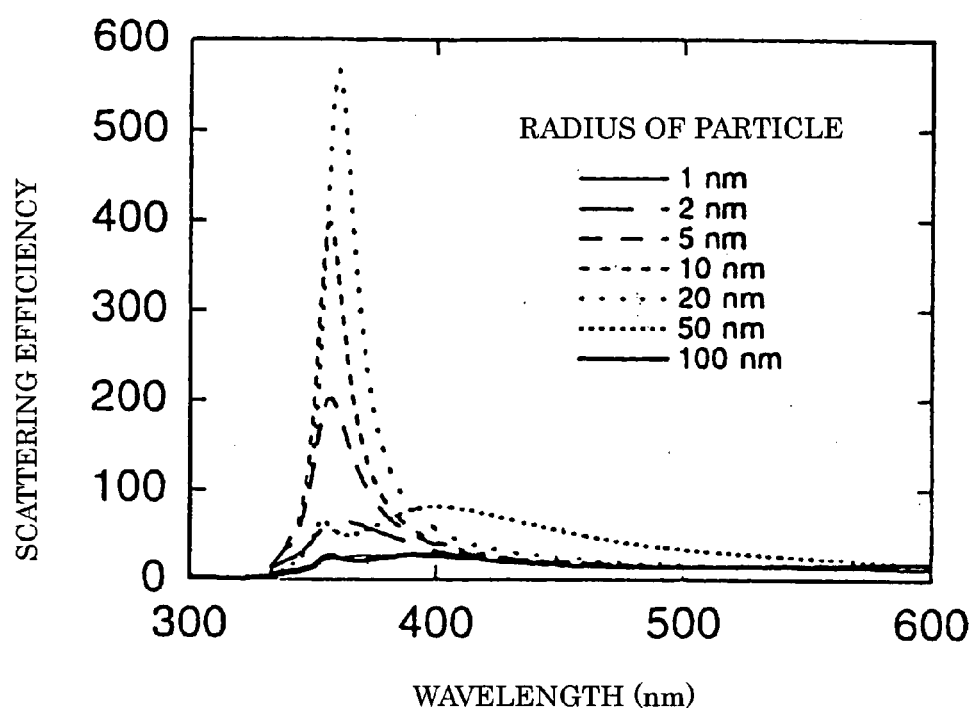
FIG. 12 is a graph showing an influence of the radius of curvature exerting on a near-field scattering efficiency.
Figure 13:
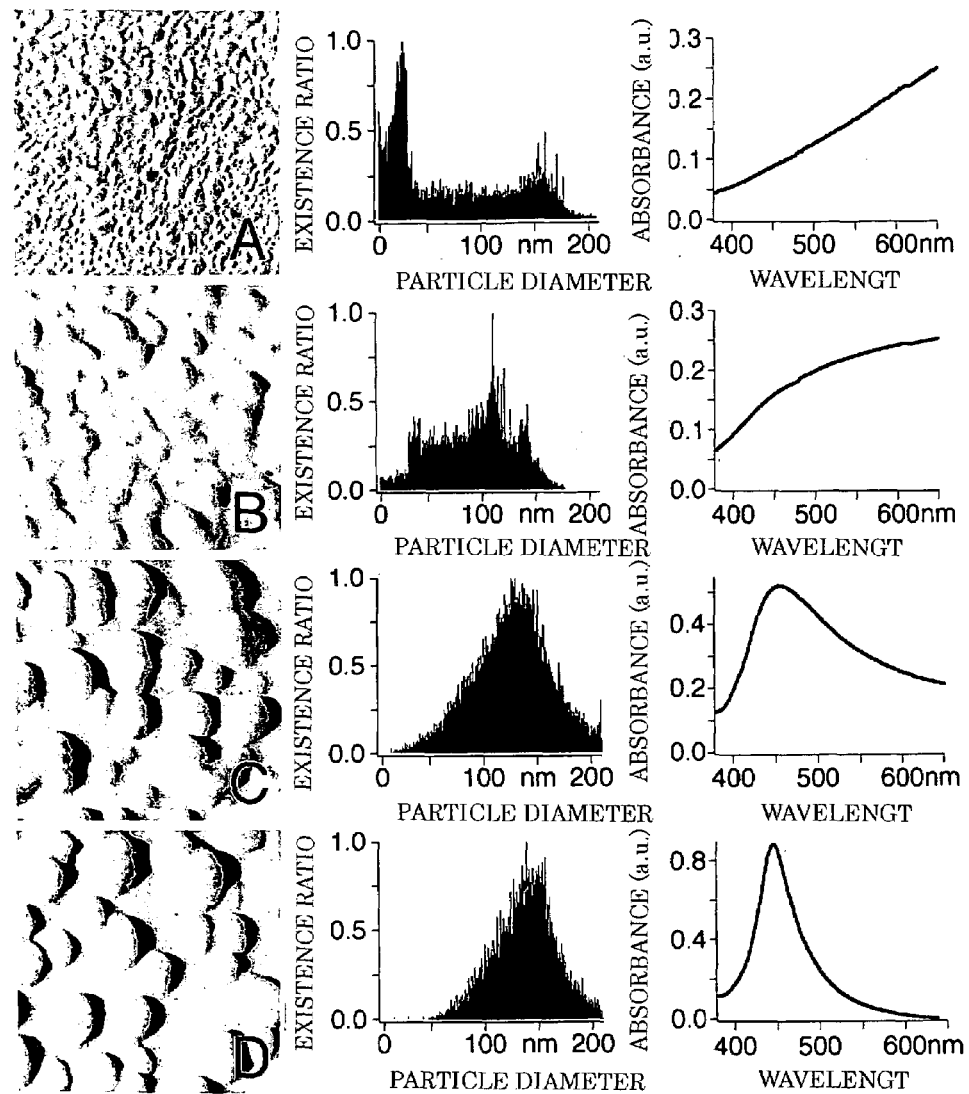
FIG. 13 shows a change in a surface plasmon absorption efficiency by a silver particle.

An scanning electron microscope photograph of the probe for the near-field microscope, which has been made by the second embodiment, is shown in FIG. 8.

Also in the present embodiment, although it is ideal that the size of the silver particle is about 20 nm in radius of curvature, if the radius of curvature is 10 nm or larger and 50 nm or smaller, it is possible to efficiently generate the surface enhanced Raman scattering, and the particle having the particle diameter of this range is included in the invention.

Further, as to an ideal film shape in the present manufacturing method, although the silver particles having the uniform particle diameter are formed in the probe part and the cantilever part without mutually adhering, such a matter is considered as well that unavoidably one part of the particles don't become the prescribed shape or are adhered due to such a fact that a concentration gradient occurs in silver nitrate by shapes of the probe. Also in this case, if one portion of the particles in the probe due to the interaction with the sample are formed in the prescribed shape without adhering, it is possible to achieve the object of the invention, the probe in which one portion of the coated particles in the probe surface due to the interaction with the sample are 10 nm or larger and 50 nm or smaller in radius of curvature and have no adhesion is included in the invention.

Additionally, the invention is not limited to the metals mentioned in the first embodiment and the second embodiment, and if it is a probe for a near-field microscope, in which one part or all of the probe at least due to the interaction of the evanescent field is coated by the metal consisting of the particles which are 10 nm or larger and 50 nm or smaller in radius of curvature and have no mutual adhesion, it is included in the invention.

Further, also the materials and the shapes of the cantilever and the probe are not limited to the above embodiments, and it is possible to use an arbitrary probe such as silicon, silicon nitride, sharpened optical fiber and metal explorer.

What is claimed is:

1. A probe for a near-field microscope comprising: a probe body is inserted into an evanescent field generated in a sample surface so that scattered light is detected by scattering the evanescent field using a probe tip of the probe body, one part or all of the probe body which interacts with the evanescent field being coated with metal particles which do not mutually adhere, each of the metal particles having a particle diameter of 10 nm or larger and a radius of curvature of 50 nm or smaller.

2. A method of manufacturing a probe for a near-field microscope, comprising: a first vapor deposition process of vapor-depositing gold-palladium as a substrate metal film on a probe body; a second vapor deposition process of vapor-depositing a metal selected from one of silver, a silver alloy, gold and a gold alloy onto the substrate metal film; and adjusting a vapor deposition time and a vapor deposition speed in the second vapor deposition process so that particles of the metal vapor-deposited in the second vapor deposition process are coated on one part or all a surface of the probe body, the metal particles comprising particles which do not mutually adhere, each of the metal particles having a particle diameter of 10 nm or larger and a radius of curvature of 50 nm or smaller.

3. A method of manufacturing a probe for a near-field microscope, comprising: proving a mixed solution by adding an aqueous solution containing an aldehyde compound as a reducing agent to an aqueous solution containing silver nitrate to thereby reduce the silver nitrate to silver; growing silver particles on a surface of a probe body by immersing the probe body into the mixed solution; and adjusting a concentration of the silver nitrate aqueous solution and a time for immersing the probe body into the mixed solution so that silver particles which do not mutually adhere are formed on one part or all of the surface of the probe body, each of the silver particles having a particle diameter of 10 nm or larger and a radius of curvature of 50 nm or smaller.

4. A scanning probe microscope having a probe according to claim 1.

* * * * *